(12) United States Patent
Huang

(10) Patent No.: US 7,166,089 B2
(45) Date of Patent: Jan. 23, 2007

(54) PLUNGER OF A SYRINGE

(76) Inventor: Ping Te Huang, No. 38, Chaofu Rd., Situn District, Taichung City (TW)

( * ) Notice: Subject to any disclaimer, the term of this patent is extended or adjusted under 35 U.S.C. 154(b) by 227 days.

(21) Appl. No.: 10/829,289

(22) Filed: Apr. 22, 2004

(65) Prior Publication Data

US 2005/0240158 A1  Oct. 27, 2005

(51) Int. Cl.
*A61M 5/315* (2006.01)
(52) U.S. Cl. ................... 604/222; 604/228
(58) Field of Classification Search ........ 604/181, 604/187, 203, 228, 218–223, 230, 110
See application file for complete search history.

(56) References Cited

U.S. PATENT DOCUMENTS 2,895,773 A * 7/1959 McConnaughey ........ 92/245
4,944,723 A * 7/1990 Haber et al. ............. 604/110
5,205,823 A * 4/1993 Zdeb ....................... 604/110

* cited by examiner

*Primary Examiner*—Nicholas D. Lucchesi
*Assistant Examiner*—Matthew F. DeSanto
(74) *Attorney, Agent, or Firm*—Egbert Law Offices

(57) ABSTRACT

A plunger of a syringe includes a shank partially movably received in a barrel of the syringe. The shank includes a first end having a thumb rest radially extending therefrom and a second end having a stub longitudinally extending from the shank. The stub includes a stopper radially extending therefrom and a mushroom-shaped connector formed on a distal end of the stub. At least one annular flange radially extends from the stub between the stopper and the mushroom-shaped connector. A rubber bulb is securely longitudinally mounted to the stub, abuts the stopper and fully contains the at least one annular flange and the mushroom-shaped connector. The rubber bulb is previously formed and connected with the shank when inject molding the shank.

1 Claim, 3 Drawing Sheets

PLUNGER OF A SYRINGE

BACKGROUND OF THE INVENTION

1. Field of the Invention

The present invention relates to plunger, and more particularly to a plunger of a syringe.

2. Description of Related Art

A conventional plunger of a syringe in accordance with the prior art shown in FIG. 3 is adapted to be slidably partially received in a barrel of the syringe, and comprises a shaft (1) and a rubber bulb (2) mounted to a first end of the shaft (1).

The shaft (1) includes a second end opposite to the first end thereof and having a thumb rest (101) laterally extending from the second end of the shaft (1). The shaft (1) includes a stopper (102) radially extending from the first end of the shaft (1) and a stub (103) longitudinally extending from the stopper (102). A flange (104) radially extends from a distal end of the stub (103) and a connector (105) centrally longitudinally extends from the distal end of the stub (103). The stub (103) and the connector (105) are tapered and each has a diameter gradually reduced relative to a free end of the connector (105).

The rubber bulb (2) includes a tapered through hole (201) centrally defined therein for receiving the stub (103) and partially receiving the connector (105). An annular groove (202) is defined in the rubber bulb (2) and laterally communicating with the tapered through hole (201) in the rubber bulb (2) for receiving the flange (104) of the plunger. The stopper (102) of the shaft (1) can prevent the first end of the shaft (1) from overly passing through the rubber bulb (2). The rubber bulb (2) abuts against an inner periphery of the barrel (3) to provide an airtight effect between the plunger and the barrel (3) during operating.

However, the conventional plunger of a syringe in accordance with the prior art includes the following disadvantages.

1. The produce rate is low and the cost is expansive when the rubber bulb (2) is mounted to the first end of the shaft (1) by manpower.

2. The rubber bulb (2) may jumps off the shaft (1) during assembling because the diameter of the through hole (201) is smaller than that of the flange (104).

The present invention has arisen to mitigate and/or obviate the disadvantages of the conventional plunger of the syringe.

SUMMARY OF THE INVENTION

The main objective of the present invention is to provide an improved plunger of a syringe, of which the shank and the rubber are securely connected to each other.

To achieve the objective, the plunger in accordance with the present invention comprises a shank partially movably received in a barrel of the syringe. The shank includes a first end having a thumb rest radially extending therefrom and a second end having a stub longitudinally extending from the shank. The stub includes a stopper radially extending therefrom and a mushroom-shaped connector formed on a distal end of the stub. At least one annular flange radially extends from the stub between the stopper and the mushroom-shaped connector. A rubber bulb is securely longitudinally mounted to the stub, abuts the stopper and fully contains the at least one annular flange and the mushroom-shaped connector. The rubber bulb is previously formed and connected with the shank when inject molding the shank.

Further benefits and advantages of the present invention will become apparent after a careful reading of the detailed description with appropriate reference to the accompanying drawings.

DETAILED DESCRIPTION OF THE INVENTION

Figure 1:
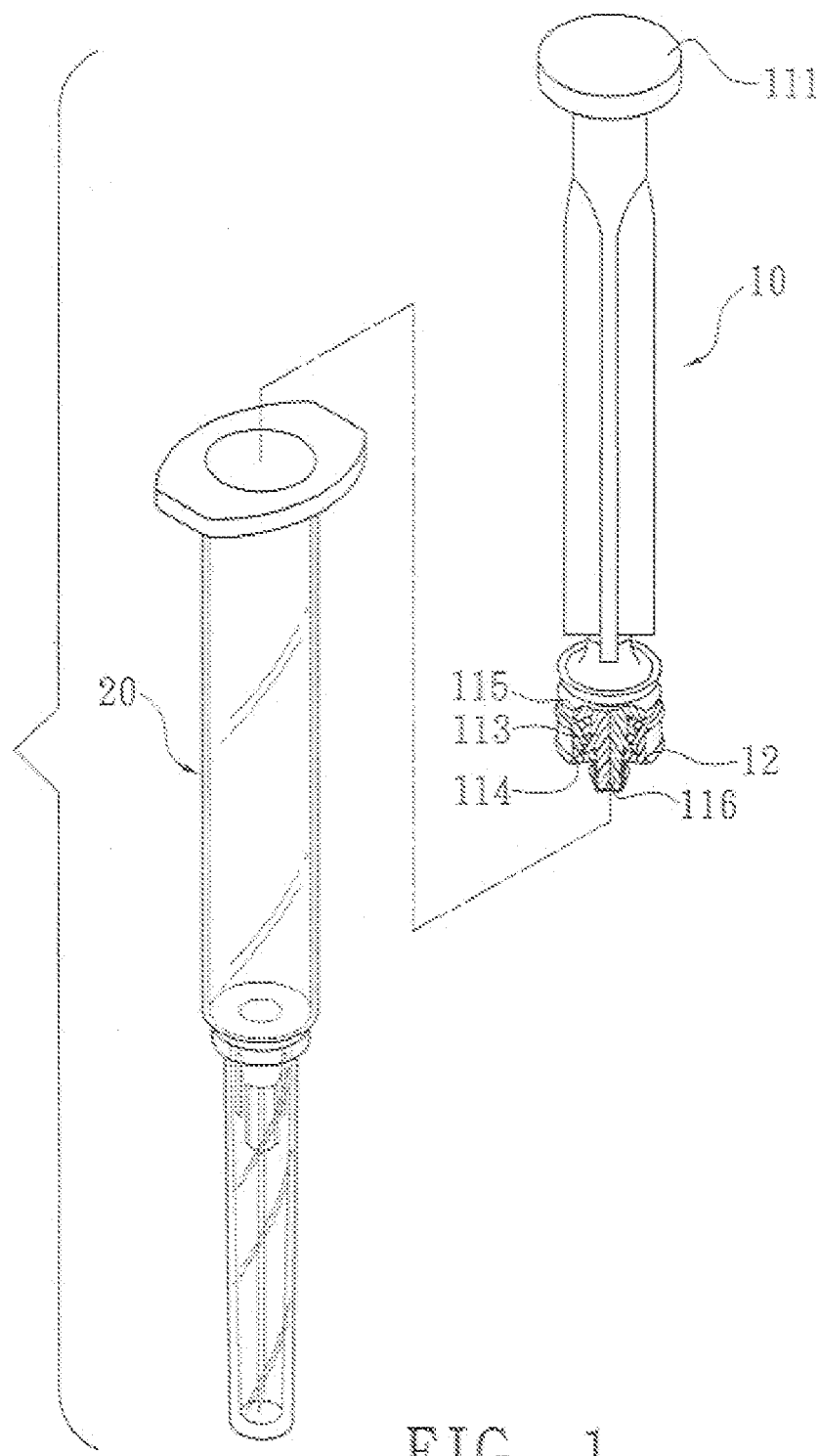
FIG. 1 is a perspective view in partial cross-section of a plunger of a syringe in accordance with the present invention.
Figure 2:
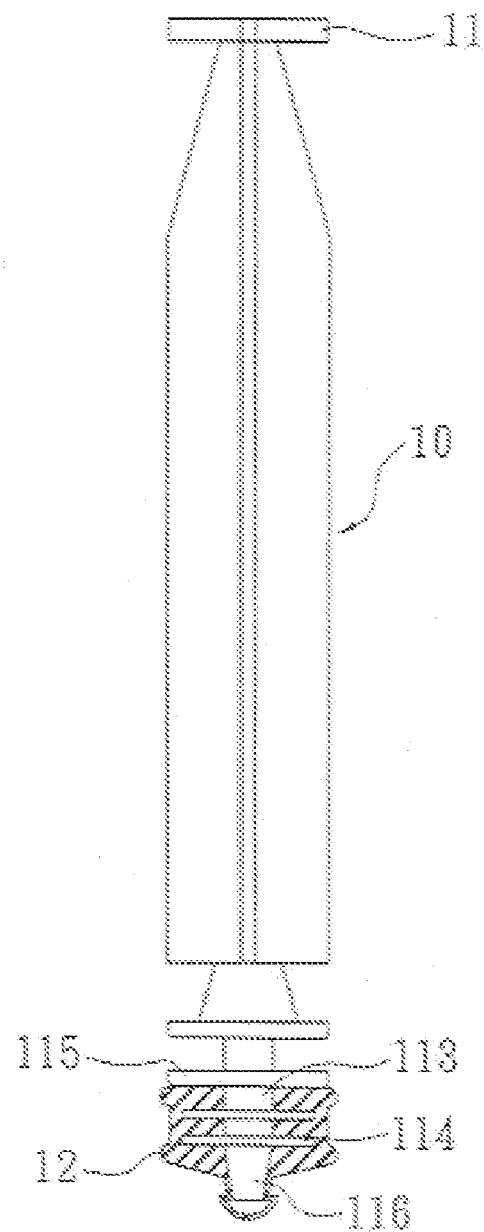
FIG. 2 is a side plan view in partial cross-section of the plunger in FIG. 1.
Figure 3:
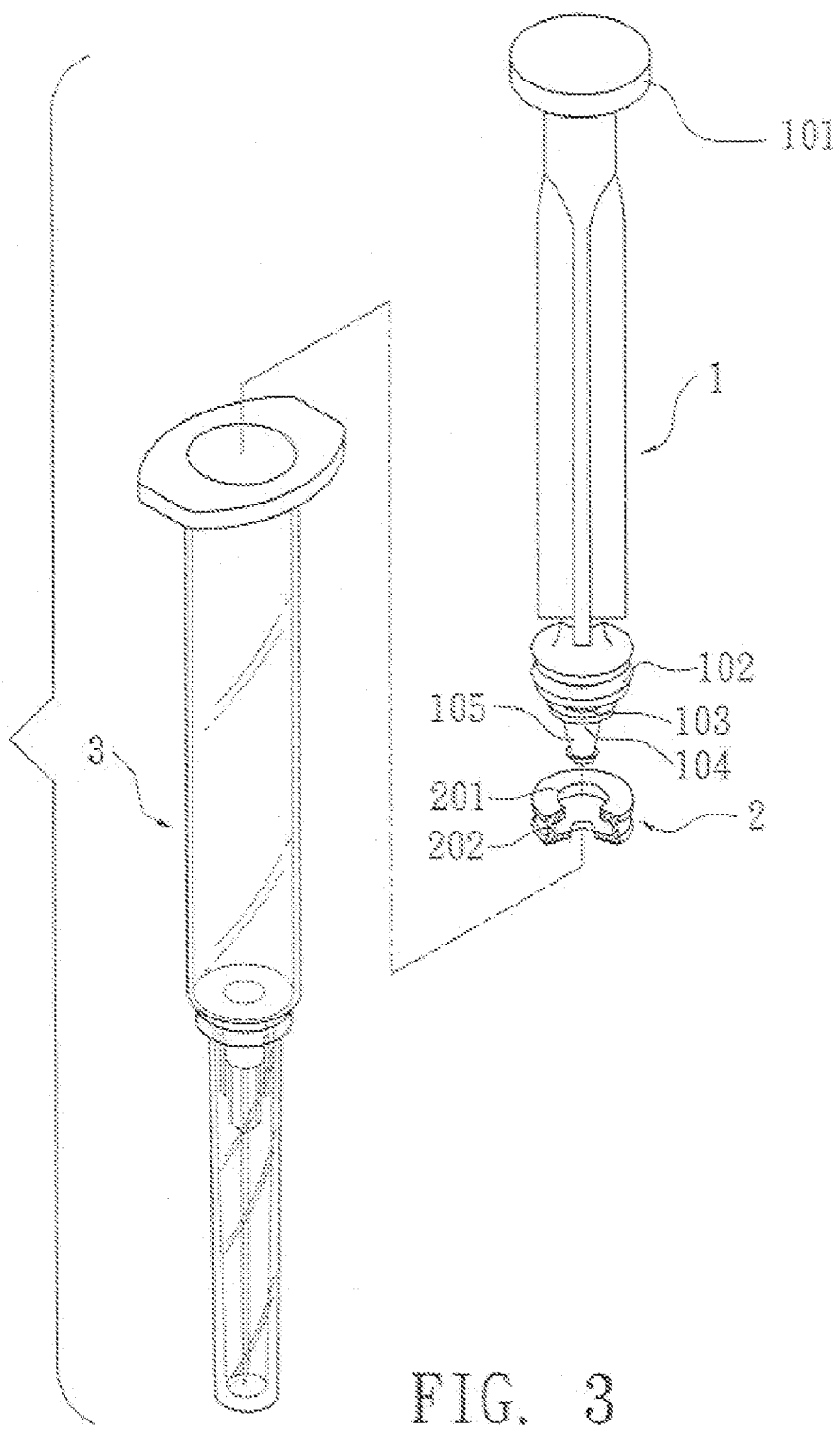
FIG. 3 is an exploded perspective view of a conventional plunger of a syringe in accordance with the prior art.

Referring to the drawings and initially to FIGS. 1 and 2, a plunger of a syringe in accordance with the present invention comprises a shank (10) adapted to be movably received in a barrel (20) of the syringe. The shank (10) includes a first end having a thumb rest (111) formed on a first end thereof for user to easily operate the plunger and a stub (113) centrally longitudinally extending from a second end of the shank (10). A mushroom-shaped connector (116) is formed on a distal end of the stub (113) for connecting to and backward pulling the needle of the syringe after syringing to achieve a purpose of safety. A stopper (115) radially extends from the stub (113) and at least one annular flange (114) radially extends form the stub (113) between the mushroom-shaped connector (116) and the stopper (115). In the preferred embodiment of the present invention, the shank (10) includes two annular flanges (114), as shown in FIGS. 1 and 2.

A rubber bulb (12) is securely mounted to the second end of the shank (10) of the plunger in accordance with the present invention. The rubber bulb (12) is previously formed and corresponding to the shape of the annular flanges (114), the stub (113) and the mushroom-shaped connector (116). The rubber bulb (12) is previously positioned in a mold that molding the plunger of the present invention. Consequently, the rubber bulb (12) fully contains the stub (113), the annular flange (114) and the mushroom-shaped connector (116). The stopper (115) can prevent the rubber bulb (12) from being backward moved during operating and the annular flange provides a good connection between the shank (10) and the rubber bulb (12).

As described above, the plunger of a syringe in accordance with the present invention has several advantages as follow.

1. The rubber bulb (12) is securely connected to the shank (10) when molding the shank (10) of the plunger. Consequently, the manual assembling process of the rubber bulb (12) is unnecessary to the present invention.

2. The manufacturing cost is reduced because the manufacturer does not need to prepare a machine for assembling the shank (10) of the plunger and the rubber bulb (12).

3. The mushroom-shaped connector (116) is coated by the rubber bulb (12) such that the mushroom-shaped connector (116) can be easily inserted into the needle of the syringe due to the material characteristic of the rubber bulb-(12) and backward pulled the needle into the barrel (20) after syringing.

Although the invention has been explained in relation to its preferred embodiment, it is to be understood that many other possible modifications and variations can be made without departing from the spirit and scope of the invention as hereinafter claimed.

What is claimed is:

1. A plunger for a syringe comprising:

a shank adapted to be partially movably received in a barrel of the syringe, said shank having a first end with a thumb rest radially extending therefrom, said shank having a secured end having a stub extending longitudinal from said shank, said stub having an exterior surface, said stub having a stopper extending radially outwardly from said exterior surface adjacent an end of said stub adjacent said shank, said stub having a mushroom-shaped connector at an opposite end of said stub, said stub having a pair of annular flanges extending radially outwardly from said exterior surface in generally parallel planar relation to each other, said pair of annular flanges positioned between said stopper and said mushroom-shaped connector; and a rubber bulb mounted on said stub so as to have an end abutting a surface of said stopper, said rubber bulb in surface-to-surface contact with said exterior surface of said stub, said rubber bulb extending between said pair of annular flanges so as to have a surface contacting said exterior surface in a space between said pair of annular flanges, said rubber bulb having a coating extending entirely over and in surface-to-surface contact with said mushroom-shaped connector.

* * * * *